United States Patent
Morino et al.

(10) Patent No.: US 6,713,500 B2
(45) Date of Patent: Mar. 30, 2004

(54) AGENT FOR CONTROLLING ANIMAL DISEASES CAUSED BY PARASITES

(75) Inventors: Kyuya Morino, Shiga (JP); Shuichi Yotsuya, Shiga (JP); Munekazu Ogawa, Shiga (JP)

(73) Assignee: Ishihara Sangyo Kaisha Ltd., Osaka (JP)

( * ) Notice: Subject to any disclaimer, the term of this patent is extended or adjusted under 35 U.S.C. 154(b) by 0 days.

(21) Appl. No.: 10/289,257

(22) Filed: Nov. 7, 2002

(65) Prior Publication Data

US 2003/0100586 A1 May 29, 2003

Related U.S. Application Data

(63) Continuation of application No. 10/048,986, filed as application No. PCT/JP00/05566 on Aug. 18, 2000, now abandoned.

(30) Foreign Application Priority Data

Aug. 19, 1999 (JP) .......................... 11-233255

(51) Int. Cl.[7] .......................... A61K 31/415
(52) U.S. Cl. ....................................... 514/396
(58) Field of Search ......................... 514/396

(56) References Cited

U.S. PATENT DOCUMENTS

| 4,659,720 A | 4/1987 | Chabala et al. |
| 5,023,336 A | 6/1991 | Shigehara et al. .......... 548/110 |

FOREIGN PATENT DOCUMENTS

| EP | 0 298 196 | 1/1989 |
| EP | 0 365 030 | 4/1990 |
| EP | 0 337 103 | 10/1999 |
| JP | 1-131163 | 5/1989 |

*Primary Examiner*—Kevin E. Weddington
(74) *Attorney, Agent, or Firm*—Oblon, Spivak, McClelland, Maier & Neustadt, P.C.

(57) ABSTRACT

The present invention provides an agent for controlling animal diseases caused by parasites, which contains, as an active ingredient, an imidazole compound represented by the formula (I):

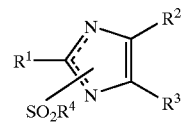

wherein $R^1$ is a cyano group, $R^2$ is an alkyl group which may be substituted, or a phenyl group which may be substituted, $R^3$ is a chlorine atom, and $R^4$ is a dimethylamino group.

18 Claims, No Drawings

AGENT FOR CONTROLLING ANIMAL DISEASES CAUSED BY PARASITES

This application is a Continuation Feb. 19, 2002, now abandoned which was originally filed as International PCT of application Ser. No. 10/048,986 Filed on application PCTJP/JP00/05566, filed Aug. 18, 2000.

TECHNICAL FIELD

The present invention relates to an agent for controlling animal diseases caused by parasites, which contains, as an active ingredient, a specific imidazole compound. Such an agent for controlling animal diseases is useful, for example, as an agent for controlling parasites such as coccidia which are parasitic on animals.

BACKGROUND ART

Heretofore, various pest controlling agents or insecticides have been employed against parasites parasitic on animals such as domestic animals, domestic poultry or companion animals. For example, for controlling coccidia which are endobiotic protozoa belonging to genus Eimeria and which are widely distributed among various domestic animals and domestic poultry such as chickens, sulfa drugs; quinolines; anti-thiamine drugs; polyether antibiotics such as monensin, salinomycin and lasalocid; and nicarbazin as a synthetic agent, have widely been used.

Further, the specific imidazole compound which is used as an active ingredient of the agent for controlling animal diseases of the present invention, is a known compound disclosed in e.g. JP-A-1-131163, JP-A-63-255269, etc. However, it has not been known to use such compound as an agent for controlling animal diseases.

DISCLOSURE OF THE INVENTION

Usually, an animal disease caused by parasites will result from parasitism of the parasites on or in the body of a host animal. The parasites which cause an animal disease, are parasitic on the body surface, stomach, intestinal tract, lung, heart, liver, blood vessels, subcutis or lymphatic tissues of domestic animals, domestic poultry or companion animals, and are likely to bring about serious problems in many cases. Animal diseases caused by parasites are likely to bring about anemia, malnutrition, asthenia, weight loss, or disorder of intestinal tract walls or other tissues or organs, and if left untreated, hosts infested with the parasites are likely to die.

Further, coccidiosis which is one of animal diseases caused by parasites, presents a serious economical loss particularly to poultry industry. Further, this is one of diseases which are problematic in breeding not only poultry but also cattle, sheep, rabbits, dogs and cats. Therefore, control of coccidiosis will bring about a substantial benefit to the poultry industry, lively stock industry and breeding of companion animals. On the basis of such a concept, the present invention provides an agent for controlling animal diseases caused by parasites.

The present inventors have conducted an extensive research for compounds which are capable of controlling animal diseases, particularly coccidiosis, caused by parasites. As a result, they have found that a certain specific imidazole compound which is known to have an agricultural application, has an effect for controlling animal diseases caused by parasites, and the present invention has been accomplished on the basis of this discovery.

Namely, the present invention provides an agent for controlling animal diseases caused by parasites, which contains, as an active ingredient, an imidazole compound represented by the formula (I):

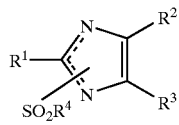

wherein $R^1$ is a cyano group, a

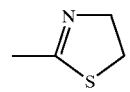

group or a

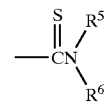

group {wherein each of $R^5$ and $R^6$ is a hydrogen atom, an alkyl group which may be substituted, an alkenyl group which may be substituted, an alkynyl group which may be substituted, a cycloalkyl group which may be substituted, an aryl group which may be substituted, or a —CO—$R^7$ group (wherein $R^7$ is an alkyl group which may be substituted, an alkoxy group which may be substituted, or an aryl group which may be substituted)}, each of $R^2$ and $R^3$ is a hydrogen atom; a halogen atom; a hydroxyl group; a nitro group; a cyano group; a thiocyanate group; a trimethylsilyl group; an alkyl group which may be substituted; a cycloalkyl group which may be substituted; an alkenyl group which may be substituted; a cycloalkenyl group which may be substituted; an alkynyl group which may be substituted; an alkoxy group which may be substituted; a cycloalkyloxy group which may be substituted; an alkenyloxy group which may be substituted; a cycloalkenyloxy group which may be substituted; an alkynyloxy group which may be substituted; an aryl group which may be substituted; an aryloxy group which may be substituted; a 5- or 6-membered aromatic heterocyclic group which may be substituted; a —$SO_nR^8$ group {wherein $R^8$ is an alkyl group which may be substituted; a cycloalkyl group which may be substituted; an alkenyl group which may be substituted; a cycloalkenyl group which may be substituted; an alkynyl group which may be substituted; an aryl group which may be substituted; a pyridyl group which may be substituted, or a —N($R^9$)$R^{10}$ group (wherein each of $R^9$ and $R^{10}$ is an alkyl group), and n is an integer of from 0 to 2}; or a

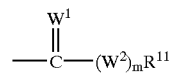

group (wherein $W^1$ is an oxygen atom or a sulfur atom, $W^2$ is an oxygen atom, a sulfur atom or —NH—, m is an integer of from 0 to 1, and $R^{11}$ is an alkyl group which may be substituted; or an aryl group which may be substituted), $R^4$ is an alkyl group which may be substituted; a cycloalkyl group which may be substituted; an aryl group which may be substituted; a thienyl group which may be substituted; a furyl group which may be substituted; or a —N($R_{12}$)$R_{13}$ group (wherein each of $R^{12}$ and $R^{13}$ is a hydrogen atom; an alkyl group which may be substituted; or an alkenyl group which may be substituted, or they form, together with the adjacent nitrogen atom, a 5- to 7-membered saturated heterocyclic group, provided that a case where $R^{12}$ and $R^{13}$ are simultaneously hydrogen atoms, is excluded), provided that a case where $R^2$ and $R^3$ are simultaneously hydrogen atoms, is excluded.

In the formula (I), the alkyl moiety contained in $R^2$ to $R^{13}$ may be one having a carbon number of from 1 to 12, and it may, for example, be a methyl group, an ethyl group, a n-propyl group, an isopropyl group, a n-butyl group, a sec-butyl group, an isobutyl group, a tert-butyl group, a n-pentyl group, a n-hexyl group, a heptyl group, an octyl group, a nonyl group or a decyl group. The cycloalkyl group represented by $R^2$, $R^3$, $R^4$, $R^5$, $R^6$ and $R^8$, may be one having a carbon number of from 3 to 7, and it may, for example, be a cyclopropyl group, a cyclobutyl group, a cyclopentyl group or a cyclohexyl group. The alkenyl group contained in $R^2$, $R^3$, $R^8$, $R^{12}$ and $R^{13}$, may be one having a carbon number of from 2 to 12, and it may, for example, be an allyl group or a geranyl group. The cycloalkenyl group represented by $R^2$, $R^3$ and $R^8$ may be one having a carbon number of from 5 to 8, and it may, for example, be a cyclopentenyl group, a cyclohexenyl group or a cyclooctenyl group. The alkynyl group contained in $R^2$, $R^3$ and $R^8$ may be one having a carbon number of from 2 to 12, and it may, for example, be a 2-propynyl group.

The aryl group which may be substituted, represented by $R^2$, $R^3$, $R^4$, $R^5$, $R^6$, $R^7$, $R^8$ and $R^{11}$, or the aryl moiety of the aryloxy group which may be substituted, represented by $R^2$ and $R^3$, may, for example, be a phenyl group or a naphthyl group. The aryl group for $R^2$, $R^3$ and $R^8$ is preferably a phenyl group or a naphthyl group. The aryl group for $R^4$, $R^5$, $R^6$, $R^7$ and $R^{11}$ is preferably a phenyl group. The aryloxy group which may be substituted, represented by $R^2$ and $R^3$, is preferably a phenoxy group. The 5- or 6-membered aromatic heterocyclic group which may be substituted, represented by $R^2$ and $R^3$, may be one containing at least one hetero atom selected from the group consisting of an oxygen atom, a sulfur atom and a nitrogen atom, in its ring, and it may, for example, be a thienyl group which may be substituted, a furyl group which may be substituted, a thiazolyl group which may be substituted, or a pyridyl group which may be substituted.

The substituent for the alkyl group which may be substituted, represented by $R^2$, $R^3$, $R^4$, $R^5$, $R^6$, $R^7$, $R^8$, $R^{11}$, $R^{12}$ and $R^{13}$; the cycloalkyl group which may be substituted, represented by $R^2$, $R^3$, $R^4$, $R^5$, $R^6$ and $R^8$; the alkenyl group which may be substituted, represented by $R^2$, $R^3$, $R^5$, $R^6$, $R^8$, $R^{12}$ and $R^{13}$; the alkynyl group which may be substituted, represented by $R^2$, $R^3$, $R^5$, $R^6$ and $R^8$; the alkoxy group which may be substituted, represented by $R^2$ and $R^3$; the alkenyloxy group which may be substituted, the alkynyloxy group which may be substituted, the cycloalkyloxy group which may be substituted, and the cycloalkenyloxy group which may be substituted, represented by $R^2$, $R^3$ and $R^7$, in the above formula (I), may, for example, be a halogen atom; an alkoxy group which may be substituted by a halogen atom; an alkylthio group which may be substituted by a halogen atom; a phenyl group which may be substituted by a halogen atom; a phenyl group substituted by an alkyl group which may be substituted by a halogen atom; or a hydroxyl group. The substituent for the aryl group which may be substituted, represented by $R^2$, $R^3$, $R^4$, $R^5$, $R^6$, $R^7$, $R^8$ and $R^{11}$; the aryloxy group which may be substituted, represented by $R^2$ and $R^3$; the pyridyl group which may be substituted, represented by $R^8$; the thienyl group which may be substituted, represented by $R^4$; the furyl group which may be substituted, represented by $R^4$; and the 5- or 6-membered aromatic heterocyclic group which may be substituted, represented by $R^2$ and $R^3$, may, for example, be a halogen atom; a nitro group; a cyano group; an alkyl group which may be substituted by a halogen atom; an alkoxyalkyl group; an alkoxy group which may be substituted by a halogen atom; a methylenedioxy group which may be substituted by a halogen atom; a —$NR^{14}R^{15}$ group (wherein each of $R^{14}$ and $R^{15}$ is a hydrogen atom, an alkyl group which may be substituted by a halogen atom, or an alkanoyl group); or a —$SO_pR^{16}$ group (wherein $R^{16}$ is an alkyl group which may be substituted by a halogen atom, and p is an integer of from 0 to 2). The number of such secondary substituents is preferably from 0 to 5. The halogen atom contained in the above $R^2$ to $R^8$ and $R^{11}$ to $R^{16}$ may be a chlorine atom, a bromine atom, a fluorine atom or an iodine atom. The alkyl moiety contained in the above $R^{14}$ to $R^{16}$ and the after mentioned $R^{17}$, may be the same one as the alkyl moiety contained in the above $R^2$ to $R^{13}$.

Further, $R^{12}$ and $R^{13}$ may, together with the adjacent nitrogen atom, form a 5- to 7-membered saturated hetero ring which may contain an oxygen atom, a sulfur atom or a nitrogen atom, such as a piperidine ring, a pyrrolidine ring, a morpholine ring or a thiomorpholine ring.

BEST MODE FOR CARRYING OUT THE INVENTION

Among the imidazole compounds of the above formula (I), preferred embodiments will be given below.

(1) The compound represented by the above formula (I), wherein $R^1$ is a cyano group, a

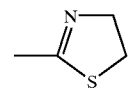

group or a

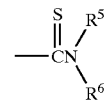

group {wherein each of $R^5$ and $R^6$ is a hydrogen atom, an alkyl group, a phenyl group which may be substituted, or a —CO—$R^7$ group (wherein $R^7$ is an alkyl group which may be substituted, or a phenyl group which may be substituted)}, each of $R^2$ and $R^3$ is a hydrogen atom; a halogen atom; a nitro group; a cyano group; a thiocyanate group; a trimethylsilyl group; an alkyl group which may be substituted; a cycloalkyl group which may be substituted; an alkenyl group which may be substituted; an alkynyl group which may be substituted; an alkoxy group which may be substituted; a phenoxy group which may be substituted; a phenyl group which may be substituted; a naphthyl group which may be substituted; a 5- or 6-membered aromatic heterocyclic group which may be substituted; a —$SO_nR^8$ group {wherein $R^8$ is an alkyl group which may be substituted; a cycloalkyl group which may be substituted; an alkenyl group which may be substituted; an alkynyl group which may be substituted; a phenyl group which may be substituted; a pyridyl group which may be substituted; a —$N(R^9)R^{10}$ group (wherein each of $R^9$ and $R^{10}$ is an alkyl group), or a naphthyl group which may be substituted, and n is an integer of from 0 to 2}; or a

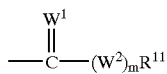

group (wherein $W^1$ is an oxygen atom or a sulfur atom, $W^2$ is an oxygen atom, a sulfur atom or —NH—, m is an integer of from 0 to 1, and $R^{11}$ is an alkyl group which may be substituted; or a phenyl group which may be substituted), $R^4$ is an alkyl group which may be substituted; a cycloalkyl group which may be substituted; a phenyl group which may be substituted; a thienyl group which may be substituted; a furyl group which may be substituted; or a —N($R^{12}$)$R^{13}$ group (wherein each of $R^{12}$ and $R^{13}$ is a hydrogen atom; an alkyl group which may be substituted; or an alkenyl group which may be substituted, or they form, together with the adjacent nitrogen atom, a 5- to 7-membered saturated heterocyclic group, provided that a case where $R^{12}$ and $R^{13}$ are simultaneously hydrogen atoms, is excluded).

(2) The compound of (1), wherein $R^1$ is a cyano group or a —C(=S)NH$R^5$ group (wherein $R^5$ is a hydrogen atom or a —C(=O)$R^7$ group, and $R^7$ is an alkyl group).

(3) The compound of (1), wherein $R^1$ is a cyano group.

(4) The compound of (1), (2) or (3), wherein each of $R^2$ and $R^3$ is a hydrogen atom; a halogen atom; a nitro group; a cyano group; an alkyl group; an alkyl group substituted by a halogen atom; an alkyl group substituted by an alkoxy group which may be substituted by a halogen atom; an alkyl group substituted by a phenyl group; an alkyl group substituted by a phenyl group which is substituted by an alkyl group; an alkyl group substituted by a phenyl group which is substituted by a halogen atom; an alkyl group substituted by a hydroxyl group; a cycloalkyl group; an alkenyl group which may be substituted by a halogen atom; an alkoxy group which may be substituted by a halogen atom; a phenyl group; a phenyl group substituted by a halogen atom; a phenyl group substituted by an alkyl group which may be substituted by a halogen atom; a phenyl group substituted by an alkoxy group which may be substituted by a halogen atom; a thienyl group; a thienyl group substituted by a halogen atom; a pyridyl group; a furyl group; a —S(O)$_n$$R^8$ group {wherein $R^8$ is an alkyl group which may be substituted by a phenyl group; a phenyl group which may be substituted by a halogen atom; a pyridyl group which may be substituted by an alkyl group substituted by a halogen atom; an alkenyl group, or a —NR$^9$R$^{10}$ group (wherein each of $R^9$ and $R^{10}$ is an alkyl group), and n is an integer of from 0 to 2}; or —C(=O)—(NH)$_m$R$^{11}$ (wherein $R^{11}$ is an alkyl group which may be substituted by a halogen atom; or a phenyl group which may be substituted by a halogen atom, and m is an integer of from 0 to 1).

(5) The compound of (1), (2) or (3), wherein $R^2$ is an alkyl group; an alkyl group substituted by a halogen atom; an alkyl group substituted by a phenyl group which may be substituted by a halogen atom; an alkenyl group which may be substituted by a halogen atom; an alkylthio group; a phenyl group; or a phenyl group substituted by a halogen atom, and $R^3$ is a halogen atom. Further preferably, $R^2$ is a methyl group, an ethyl group, a n-propyl group, an isopropyl group, a n-butyl group, an isobutyl group, a n-pentyl group, a 3-chloro-n-propyl group, a 4-chloro-n-butyl group, an allyl group, an ethylthio group, a phenyl group, a 2-chlorophenyl group, a 2-fluorophenyl group, a benzyl group or a 2-fluorobenzyl group, and $R^3$ is a chlorine atom or a bromine atom.

(6) The compound of (1), (2), (3), (4) or (5), wherein $R^4$ is a —N(CH$_3$)$_2$ group.

(7) The compound of (1), wherein $R^1$ is a cyano group, $R^2$ is an alkyl group which may be substituted, or a phenyl group which may be substituted, $R^3$ is a chlorine atom, and $R^4$ is a dimethylamino group.

A particularly preferred imidazole compound is the compound of the above-preferred embodiment (7), which includes the following compounds.

4-chloro-2-cyano-1-dimethylsulfamoyl-5-(4-methylphenyl)imidazole (compound No. 1)

4-chloro-2-cyano-1-dimethylsulfamoyl-5-(4-methoxyphenyl)imidazole (compound No. 2)

4-chloro-2-cyano-1-dimethylsulfamoyl-5-(4-ethylphenyl)imidazole (compound No. 3)

4-chloro-2-cyano-1-dimethylsulfamoyl-5-(3-methyl-4-methoxyphenyl)imidazole (compound No. 4)

4-chloro-2-cyano-1-dimethylsulfamoyl-5-(4-ethyl-α-fluorobenzyl)imidazole (compound No. 5)

The imidazole compound of the above formula (I) can be prepared by methods disclosed in e.g. JP-A-1-131163 and JP-A-8-208623.

The agent for controlling animal diseases caused by parasites of the present invention is effective against (1) parasites parasitic on the exterior of a host animal, such as, acarus, such as mange mite, mesostigmatid mites, sarcoptic mange mite (*Sarcoptes scabiei*), trombiculid mites, New Zealand cattle tick (*Haemaphyalis longicornis*) and southern cattle tick (*Boophilus microplus*); fleas such as cat flea (*Ctenocephalides felis*), dog flea (*Ctenocephalides canis*), northern rat flea (*Nosopsyllus fasciatus*), oriental rat flea (*Xenopsylla cheopis*) and human flea (*Pulex irritans*); sucking lice such as short-nosed cattle louse (*Haematopinus eurysternus*), horse sucking louse (*Haematopinus asini*), sheep lice, long-nosed cattle louse (*Linognathus vituli*) and head louse (*Pediculus capitis*); biting lice such as dog biting louse (*Trichodectes canis*); blood-sucking dipterous insects such as horse fly (*Tabanus trigonus*), biting midges (*Culicoides schultzei*) and blackfly (*Simulium ornatum*); and (2) parasites parasitic in the body of a host animal, such as, nematodes such as lung worms, whipworm (*Trichuris trichiura*), tuberous worm, gastric parasites, ascaris and filarioidea; tapeworms; flukes; and protozoa such as coccidia, malarial parasite (*Plasmodium malariae*), intestinal sarcocyst, Toxoplasma and cryptosporidium. Among these parasites, it is particularly effective against parasites parasitic in the body of a host animal, and among them, it is especially effective against protozoa. Further, among protozoa, it is particularly effective against coccidia. Further, among coccidia, it is most effective against coccidia parasitic on domestic poultry (such as fowls, ducks, geese or turkeys). The coccidia parasitic on domestic poultry include, for example, *Eimeria tenella, Eimeria acervulina, Eimeria brunetti, Eimeria maxima, Eimeria mitis, Eimeria mivati, Eimeria necatrix* and *Eimeria praecox*.

The compound of the formula (I) may be used as it is. However, it may be used as formulated together with a suitable vehicle into a formulation such as a powder, a granule, a tablet, a dusting powder, a capsule, a pre-mix, a solution or an emulsion. The suitable vehicle may be one which is commonly used as a feed additive, and it may, for example, be lactose, sucrose, glucose, starch, wheat powder, corn powder, soybean meal, degreased rice bran, calcium carbonate or other commercially available feed material. Further, the compound of the present invention can be used, together with a vehicle, in combination with various vitamins, minerals, amino acids, enzyme drugs, antifebriles, sedatives, antiphlogistics, bactericides, colorants, aromatizing agents, preservatives, etc. The dose of the compound of the formula (I) varies depending upon the administration method, the purpose of administration, the diseased degree, etc. However, it is usually administered as mixed in a feed in a concentration of at least 0.1 ppm.

The compound of the above formula (I) may sometimes change to a compound of the formula (II):

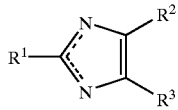

(wherein $R^1$, $R^2$ and $R^3$ are as defined above). Such a compound of the formula (II) will also act as an agent for controlling animal diseases caused by parasites in the same manner as the compound of the formula (I) in the body of an animal.

The compound of the above formula (II) is disclosed as an intermediate of the compound of the formula (I) in JP-A-1-131163. This compound can be produced by e.g. the methods disclosed in e.g. JP-A-1-131163, JP-A-4-59766, JP-A-7-215946, JP-A-7-252233, JP-A-7-252234, JP-A-7-309843 and JP-A-8-225539.

EXAMPLES

Now, the present invention will be described in further detail with reference to the following Examples, but these Examples by no means restrict the present invention.

Test Examples

Chicks were infested with *Eimeria tenella* of wild type to obtain fresh immature oocysts. The obtained fresh immature oocysts were exposed to a solution of each test substance having a predetermined concentration for 10 or 30 minutes. The exposed immature oocysts were centrifuged at 1500 $min^{-1}$ for 5 minutes, and the supernatant was removed. Then, a 2% potassium bichromate aqueous solution was added, and sporulation was carried out at 25° C. for 4 days, whereupon the ratio of mature oocysts (sporulated oocysts) to the number of observed oocysts, was calculated. Further, the mortality of oocysts was obtained by the following formula, and the results are shown in Table 1.

Mortality of oocysts={1−(sporulation rate with exposure to test substance)/(sporulation rate without exposure to test substance)}×100

TABLE 1

| ppm | Mortality of oocysts (%) | | | | | | | |
|---|---|---|---|---|---|---|---|---|
| Test | Exposure time: 10 min | | | | Exposure time: 30 min | | | |
| substance | 0* | 0.1 | 1 | 10 | 0* | 0.1 | 1 | 10 |
| Compound No. 1 | 2.5 | 43.8 | 36.9 | 42.5 | 1.9 | 51.1 | 80.3 | 87.9 |
| Compound No. 5 | 2.5 | 34.4 | 30.0 | 75.0 | 1.9 | 71.3 | 75.2 | 72.6 |

Note:
*indicates that only 10% dimethylsulfoxide was used.

Industrial Applicability

According to the present invention, the specific imidazole compound can be presented as an agent for controlling animal diseases caused by parasites.

What is claimed is:

1. A method for controlling animal diseases caused by parasites, which comprises administering to an animal in need thereof a composition comprising an imidazole compound represented by the formula (I):

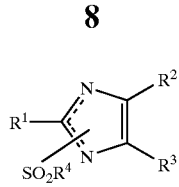

wherein $R^1$ is a cyano group, a

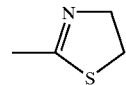

group or a

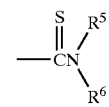

group {wherein each of $R^5$ and $R^6$ is a hydrogen atom, an alkyl group which may be substituted, an alkenyl group which may be substituted, an alkynyl group which may be substituted, a cycloalkyl group which may be substituted, an aryl group which may be substituted, or a —CO—$R^7$ group (wherein $R^7$ is an alkyl group which may be substituted, an alkoxy group which may be substituted, or an aryl group which may be substituted)}, each of $R^2$ and $R^3$ is a hydrogen atom; a halogen atom; a hydroxyl group; a nitro group; a cyano group; a thiocyanate group; a trimethylsilyl group; an alkyl group which may be substituted; a cycloalkyl group which may be substituted; an alkenyl group which may be substituted; a cycloalkenyl group which may be substituted; an alkynyl group which may be substituted; an alkoxy group which may be substituted; a cycloalkyloxy group which may be substituted; an alkenyloxy group which may be substituted; a cycloalkenyloxy group which may be substituted; an alkynyloxy group which may be substituted; an aryl group which may be substituted; an aryloxy group which may be substituted; a 5- or 6-membered aromatic heterocyclic group which may be substituted; a —$SO_nR^8$ group {wherein $R^8$ is an alkyl group which may be substituted; a cycloalkyl group which may be substituted; an alkenyl group which may be substituted; a cycloalkenyl group which may be substituted; an alkynyl group which may be substituted; an aryl group which may be substituted; a pyridyl group which may be substituted, or a —N($R^9$)$R^{10}$ group (wherein each of $R^9$ and $R^{10}$ is an alkyl group), and n is an integer of from 0 to 2}; or a

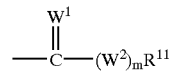

group (wherein $W^1$ is an oxygen atom or a sulfur atom, $W^2$ is an oxygen atom, a sulfur atom or —NH—, m is an integer of from 0 to 1, and $R^{11}$ is an alkyl group which may be substituted; or an aryl group which may be substituted), $R^4$ is an alkyl group which may be substituted; a cycloalkyl group which may be substituted; an aryl group which may be substituted; a thienyl group which may be substituted; a furyl group which may be substituted; or a —N($R^{12}$)$R^{13}$ group (wherein each of $R^{12}$ and $R^{13}$ is a hydrogen atom; an alkyl group which may be substituted; or an alkenyl group which may be substituted, or they form, together with the adjacent nitrogen atom, a 5- to 7-membered saturated heterocyclic group, provided that $R^{12}$ and $R^{13}$ are not simultaneously hydrogen atoms), and provided that $R^2$ and $R^3$ are not simultaneously hydrogen atoms.

2. The method according to claim 1, wherein $R^1$ is a cyano group, a

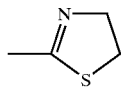

group or a

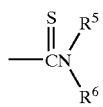

group {wherein each of $R^5$ and $R^6$ is a hydrogen atom, an alkyl group, a phenyl group which may be substituted, or a —CO—$R^7$ group (wherein $R^7$ is an alkyl group which may be substituted, or a phenyl group which may be substituted)}, each of $R^2$ and $R^3$ is a hydrogen atom; a halogen atom; a nitro group; a cyano group; a thiocyanate group; a trimethylsilyl group; an alkyl group which may be substituted; a cycloalkyl group which may be substituted; an alkenyl group which may be substituted; an alkynyl group which may be substituted; an alkoxy group which may be substituted; a phenoxy group which may be substituted; a phenyl group which may be substituted; a naphthyl group which may be substituted; a 5- or 6-membered aromatic heterocyclic group which may be substituted; a —SO$_n$R$^8$ group {wherein $R^8$ is an alkyl group which may be substituted; a cycloalkyl group which may be substituted; an alkenyl group which may be substituted; an alkynyl group which may be substituted; a phenyl group which may be substituted; a pyridyl group which may be substituted; a —N(R$^9$)R$^{10}$ group (wherein each of $R^9$ and $R^{10}$ is an alkyl group), or a naphthyl group which may be substituted, and n is an integer of from 0 to 2}; or a

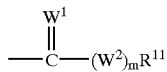

group (wherein $W^1$ is an oxygen atom or a sulfur atom, $W^2$ is an oxygen atom, a sulfur atom or —NH—, m is an integer of from 0 to 1, and $R^{11}$ is an alkyl group which may be substituted; or a phenyl group which may be substituted), $R^4$ is an alkyl group which may be substituted; a cycloalkyl group which may be substituted; a phenyl group which may be substituted; a thienyl group which may be substituted; a furyl group which may be substituted; or a —N(R$^{12}$)R$^{13}$ group (wherein each of $R^{12}$ and $R^{13}$ is a hydrogen atom; an alkyl group which may be substituted; or an alkenyl group which may be substituted, or they form, together with the adjacent nitrogen atom, a 5- to 7-membered saturated heterocyclic group, provided that $R^{12}$ and $R^{13}$ are not simultaneously hydrogen atoms).

3. The method according to claim 1, wherein $R^1$ is a cyano group, $R^2$ is an alkyl group which may be substituted, or a phenyl group which may be substituted, $R^3$ is a chlorine atom, and $R^4$ is a dimethylamino group.

4. The method according to claim 1, wherein the parasites are parasitic in the body of a host animal.

5. The method according to claim 4, wherein the parasites are protozoa.

6. The method according to claim 5, wherein the protozoa are coccidia.

7. The method according to claim 6, wherein the coccidia are coccidia of a domestic animal.

8. The method according to claim 1, wherein the imidazole compound is 4-chloro-2-cyano-1-dimethylsulfamoyl-5-(4-methylphenyl) imidazole.

9. The method according to claim 1, wherein the imidazole compound is 4-chloro-2-cyano-1-dimethylsulfamoyl-5-(4-methoxyphenyl) imidazole.

10. The method according to claim 1, wherein the imidazole compound is 4-chloro-2-cyano-1-dimethylsulfamoyl-5-(4-ethylphenyl) imidazole.

11. The method according to claim 1, wherein the imidazole compound is 4-chloro-2-cyano-1-dimethylsulfamoyl-5-(3-methyl-4-methoxyphenyl) imidazole.

12. The method according to claim 1, wherein the imidazole compound is 4-chloro-2-cyano-1-dimethylsulfamoyl-5-(4-ethyl-α-fluorobenzyl) imidazole.

13. The method according to claim 1, wherein the parasites are parasitic on the exterior of the body of a host animal.

14. The method according to claim 13, wherein the parasites are selected from the group consisting of acarus, mange mite, mesostigmatid mites, sarcoptic mange mites, trombiculid mites, New Zealand cattle ticks, fleas, cat fleas, dog fleas, northern rat fleas, oriental rat fleas, human fleas, sucking lice, short-nosed cattle lice, horse sucking lice, sheep lice, long-nosed cattle lice, head lice, dog biting lice, horse flies, biting midges, and black flies.

15. The method according to claim 1, wherein the composition is in the form of a powder, a granule, a tablet, a dusting powder, a capsule, a solution, or an emulsion.

16. The method according to claim 1, wherein said composition further comprises an additive selected from the group consisting of feed additives, vitamins, minerals, amino acids, enzyme drugs, antifebriles, sedatives, antiphlogistics, bacteriacides, colorants, aromatizing agents, and preservatives.

17. The method according to claim 16, wherein the feed additives comprise at least one additive selected from the group consisting of lactose, sucrose, glucose, starch, wheat powder, corn powder, soybean meal, degreased rice bran, and calcium carbonate.

18. The method according to claim 1, wherein the imidazole compound is administered at a concentration of at least 0.1 ppm in feed.

* * * * *